United States Patent [19]

Raleigh et al.

[11] Patent Number: 4,980,156

[45] Date of Patent: Dec. 25, 1990

[54] ANTIPERSPIRANT COMPOSITIONS

[75] Inventors: William J. Raleigh, Rensselaer; Raymond J. Thimineur, Scotia; Anthony A. Zotto, Troy, all of N.Y.

[73] Assignee: General Electric Company, Waterford, N.Y.

[21] Appl. No.: 282,655

[22] Filed: Dec. 12, 1988

[51] Int. Cl.$^5$ .......................... A61K 7/32; A61K 7/34; A61K 7/38

[52] U.S. Cl. ...................................... 424/66; 424/68; 514/938

[58] Field of Search ................ 424/65, 66, 68, DIG. 5

[56] References Cited

U.S. PATENT DOCUMENTS

| | | | |
|---|---|---|---|
| 2,846,458 | 8/1958 | Haluska | 260/448.2 |
| 3,234,252 | 2/1966 | Pater | 260/448.2 |
| 3,427,271 | 2/1969 | McKellar | 260/29.2 |
| 3,657,305 | 4/1972 | Morehouse | 260/448.2 |
| 4,047,958 | 9/1977 | Yoneyama | 96/87 |
| 4,122,029 | 10/1978 | Gee et al. | 252/309 |
| 4,268,499 | 5/1981 | Keil | 424/68 |
| 4,421,656 | 12/1983 | Donatelli et al. | 252/8.5 |
| 4,704,271 | 11/1987 | Hourihan et al. | 424/66 |
| 4,719,103 | 1/1988 | Krevald et al. | 424/66 |
| 4,722,836 | 2/1988 | Geary et al. | 424/66 |
| 4,724,139 | 2/1988 | Palinczar | 424/66 |
| 4,725,431 | 2/1988 | Hourihan et al. | 424/66 |
| 4,732,754 | 3/1988 | Krevald | 424/66 |

*Primary Examiner*—Dale R. Ore

[57] ABSTRACT

An improved dry-feeling antiperspirant composition is provided which comprises an aqueous solution of an astringent emulsified in a volatile silicon fluid, the emulsion being stabilized by a combination of a long-chain alkyl modified polysiloxane-polyoxyalkylene copolymer and an organic surfactant having an HLB value from 8 to 18.

3 Claims, No Drawings

ANTIPERSPIRANT COMPOSITIONS

BACKGROUND OF THE INVENTION

This invention relates to antiperspirant compositions of the so-called dry-feeling type, comprising an emulsion of an aqueous solution of an astringent in a volatile, water-insoluble liquid and having improved efficacy.

Antiperspirant compositions are well known in the cosmetic art. These compositions are formulated as aerosols, gels, sticks, creams, pump sprays and lotions and comprise an astringent, typically comprising one or more zirconium salts and/or aluminum salts, in various forms such as a dry, impalpable powder, an alcohol solution or an aqueous solution. Of these various forms of astringents the aqueous solution is generally considered to be the most effective antiperspirant.

However, an antiperspirant composition having water as the continuous phase, such as an aqueous solution of an astringent, or an oil-in-water type emulsion thereof, is less desirable than a composition comprising a dry powder or an alcohol solution thereof because it tends to feel wet when applied to the human skin and to go through a tacky state during the drying period after application.

U.S. Pat. No. 4,122,029 discloses water-in-oil type compositions having broad utility and comprising a polydiorganosiloxane-polyoxyalkylene copolymer and a water-in-oil type surfactant. When formulated as an antiperspirant emulsion of an aqueous solution of an astringent such as aluminum chlorhydrate emulsified in a volatile, non-aqueous continuous phase, these compositions have a desirable dry feeling when applied to the human skin and do not exhibit the wet-and-tacky effect noted above.

U.S. Pat. No. 4,268,499 discloses compositions described as having greater efficacy than those of U.S. Pat. No. 4,122,029. The efficacy was determined by applying compositions to subjects' wrists and measuring the time required for the compositions to begin to dry and turn white. This "whitening" is a characteristic of antiperspirants of the "dry-feeling" type which the consuming public has found objectionable because of the visibility of the white area on uncovered skin, and the tendency of the active ingredient to fall off the skin, which reduces the efficiency of the product and may also cause unsightly stains if the active ingredient falls on the fabric of clothing.

SUMMARY OF THE INVENTION

It is an object of this invention to provide antiperspirant emulsion compositions of the water-in-oil type which have improved efficacy. It is a further object of this invention to provide improved antiperspirant compositions comprising an emulsion of aqueous aluminum chlorhydrate in a volatile silicone fluid.

The present invention achieves these objects, and others which will be obvious upon consideration of this disclosure, by the use of a long-chain hydrocarbon-modified organosilicon water-in-oil type surfactant in formulating anti-perspirant compositions. The resulting compositions are stable, exhibiting the desired "dry" feeling, and show much less whitening of the skin on drying.

DETAILED DESCRIPTION OF THE INVENTION

This invention relates to an improved antiperspirant emulsion composition comprising (a) from about 89.5 to about 50 parts by weight of an aqueous solution of an astringent as a discontinuous phase;

(b) from about 10 to about 45 parts by weight of a volatile liquid having a normal boiling point of less than 250° C. as a continuous phase, said volatile liquid being selected from methylsiloxane fluids having the average unit formula $$(CH_3)_a SiO_{(4-a)/2}$$

wherein a has an average value of from 2 to 3 inclusive;

(c) from about 0.4 to about 6 parts by weight of a polydiorganosiloxane-polyoxyalkylene copolymer of the general formula $$MD_x D'_y D''_z M$$

wherein

D is $(CH_3)_2 SiO_{2/2}$,

D' is $(CH_3) R^1 SiO_{2/2}$, where $R^1$ is an alkyl group having from 6 to 30 carbon atoms, D'' is $(CH_3) R^2 SiO_{2/2}$, where $R^2$ is a polyoxyalkylene ether residue of the formula $$-(R^4)_p-(OR^3)_n-OR^5$$

wherein each individual $R^3$ is a substituted or unsubstituted alkylene radical having 2 to 6 carbon atoms, $R^4$ is a substituted or unsubstituted alkylene radical having 2 to 20 carbon atoms, and $R^5$ is hydrogen or a substituted or unsubstituted hydrocarbon radical of from 1 to about 12 carbon atoms, and n has a value from about 5 to about 20, p has a value of zero or 1, M is $(CH_3)_2 R^6 SiO_{2/2}$, where $R^6$ may be an alkyl group having from 1 to 30 carbon atoms or $R^2$, x has an average value of from about 10 to about 400, y has an average value of from 1 to about 200, z has an average value of from 1 to about 100; and x+y+z has an average value of from about 12 to about 400, the proviso that the weight ratio of $R^2$ to polysiloxane absent $R^2$ is from greater than 15/85 to less than 35/65; and (d) from about 0.1 to about 3 parts by weight of an organic oil-in-water type surfactant having an HLB value of from 8 to 18 inclusive, the total of (a) plus (b) plus (c) plus (d) being 100 parts by weight.

Component (a) is an aqueous solution of any water-soluble astringent antiperspirant agent. Examples of well-known astringents include aluminum, hafnium and zirconium salts, such as zirconyl hydroxide halides, aluminum zirconium chloride, zirconium-aluminum lactate, basic aluminum halides such as $Al_2(OH)_5Cl$, aluminum bromide and the several water, alcohol or glycine complexes thereof.

The amount of astringent that is dissolved in water to form component (a) may vary widely and is not critical; however, certain practical limitations exist. On the one hand an efficacious anti-perspirant composition would contain sufficient astringent to provide sweat reduction, although compositions containing less astringent are useful as personal care compositions. Preferably, the anti-perspirant composition comprises approximately 15–30 weight percent astringent. On the other hand, it is desirable to maximize the amount of water in the anti-perspirant formulation without negating utility, for obvious economic reasons. Depending on the particular astringent that is used, component (a) may vary in concentration from as little as one part by weight astringent per three parts by weight water up to a saturated aqueous solution of the astringent.

The volatile liquid (b) is a fluid selected from the methylsiloxane fluids having a normal, i.e. atmospheric pressure, boiling point of less than 250° C.

The volatile methylsiloxane fluid (b) has the average unit formula $$(CH_3)_aSiO_{(4-a)/2}$$

where a has an average value of from 2 to 3 and consists of siloxane units selected from the group consisting of $(CH_3)_3SiO_{1/2}$ $(CH_3)SiO_{2/2}$, $CH_3SiO_{3/2}$ and $SiO_{4/2}$ units. Preferably, the volatile methylsiloxane fluid consists essentially of dimethylsiloxane units, and optionally, trimethylsiloxane units. Of particular value as volatile liquid (b) are the cyclic siloxanes of the general formula $[(CH_3)_2SiO]_b$ and the linear siloxanes of the general formula $(CH_3)_3SiO[(CH_3)_2SiO]_cSi(CH_3)_3$, and their mixtures, wherein b is an integer of from 3 to 6 and c is an integer of from 0 to 4. A highly preferred methylsiloxane fluid is a mixture of said cyclic siloxanes wherein a major portion is tetramer (b=4) or (b=5).

Component (c) is a long chain hydrocarbon-modified polydiorganosiloxane polyoxyalkylene copolymer containing polydimethylsiloxy groups, on average at least one long-chain alkyl (methyl) siloxy group, and on average at least one polyoxyalkylene group, having the general formula $$MD_xD'D''M$$

wherein

D is $(CH_3)_2 SiO_{2/2}$;

D' is $(CH_3) R^1SiO_{2/2}$, where $R^1$ is an alkyl group having from 6 to 30 carbon atoms, preferably about 8 to 18 carbon atoms, and most preferably about 10 to 12 carbon atoms;

D'' is $(CH_3)R^2SiO_{2/2}$, where $R^2$ is a polyoxyalkylene ether residue of the formula $$-(R^4)_p-(OR_3)_n-OR_5$$

wherein each individual $R^3$ is a substituted or unsubstituted alkylene radical having 2 to 6 carbon atoms, $R^4$ is a substituted or unsubstituted alkylene radical having 2 to 20 carbon atoms, and $R^5$ is hydrogen or a substituted or unsubstituted hydrocarbon radical of from 1 to about 12 carbon atoms, and n has an average from about 5 to about 20, p has a value of zero or 1, M is $(CH_3)_2R^6SiO_{2/2}$, where $R^6$ may be an alkyl group having from 1 to 30 carbon atoms or $R^2$;

x bas an average value of from about 10 to about 400;

y has an average value of from 1 to about 200;

z has an average value of from 1 to about 100; and x+y+z has an average value of from about 12 to about 400, with the proviso that the weight ratio of $R^2$ to polysiloxane absent $R^2$ is from greater than 15/85 to less than 35/65.

The polyoxyalkylene segments of the copolymer (c) consist essentially of oxyethylene units of the formula $-CH_2CH_2O-$, alone or in combination with oxyalkylene units of the formula $-C_nH_{2n}O-$, where $n=3-6$, an average of at least half of the oxyalkylene units of the polyoxyalkylene segments being oxyethylene units. Suitable emulsions of this invention are not formed when the polyoxyalkylene segments contain more than 50 mol percent of the relatively hydrophobic higher oxyalkylene units. The polyoxyalkylene segments thus correspond to the formula $(-CH_2CH_2O-)_r$, $(C_nH_{2n}O)_q$ wherein the oxyalkylene units may be arranged in any suitable fashion such as random, alternating and block. The average values of r and q are such that $r \geq q$ and the sum of $r+q=n$, where n has an average value from about 5 to about 20 as stated above. The preferred polyoxyalkylene segments consist solely of oxyethylene units. It is critical herein that the number of repeating units of $-OR^3-$, i.e. the value of n, be between about 5 and 20. Thus, in the case of ethylene oxide as the repeating unit, the molecular weight of $R^2$ should be less than about 900. The preferred value of n is from 10 to 15, which likewise for ethylene oxide provides a molecular weight for $R^2$ of no more than about 700.

$R^4$ is the group which bonds the polyoxyalkylene segment to the polysiloxane. $R^4$ may be $-CH_2CH_2CH_2-$, $-CH_2CH_2-$, $-CH_2CH_2CH_2CH_2-$, etc. Preferably, $R^4$ is $-CH_2CH_2CH_2-$. When "p" is zero the segments are joined by $-O-$ which is the product of a condensation reaction between a condensable substituent on the polysiloxane and a condensable end group on polyalkylene oxide. Although component (c) is not soluble in water and therefore is not subjected to vigorous hydrolysis conditions in the compositions of this invention, it is preferred that "p" be one, avoiding the use of the hydrolyzable carbon-oxygen-silicon bond to link the polyoxyalkylene residue to the polysiloxane chain.

$R^5$ is the terminal group of the polyalkylene ether. The type of $R^5$ is not critical and may be selected from hydrogen, methyl, ethyl, propyl, butyl, phenyl, acetyl, etc. Preferably $R^5$ is hydrogen.

The radical $R^6$ of the end-blocking group M may be a lower alkyl group, or else an alkyl group derived from the olefin used to form the R' groups of the element $D^1$ or an $R^2$ group derived from the polyether used to form $R^2$ groups when the polysiloxane containing silicon hydride groups is end-blocked with dimethylhydrogen siloxy groups. It is preferred however to utilize a polysiloxane starting material which is end-blocked with trimethylsiloxy groups, in which case $R^6$ is methyl.

The copolymers (c) may be prepared by any suitable method; several are disclosed in the organosilicon art. A preferred method for preparing the polydiorganosiloxane component comprises reacting a methyl siloxane having terminal and/or in-chain silicon-bonded hydrogen atoms with an olefin having from 6 to 30 carbon atoms, such as 1-octene, 1-octadecene or -dodecene, and an olefinically terminated polyoxyalkylene, such as $CH_2=CHCH_2O(CH_2CH_2O)_p(C_nH_{2n}O)_qH$ in the presence of a platinum-containing catalyst, such as $H_2PtCl_6.6H_2O$. In this preferred method the olefin and the olefinically terminated polyoxyalkylene are most preferably reacted sequentially, olefin first, with the methylsiloxane containing silicon-bonded hydrogen radicals. The disclosures of U.S. Pat. Nos. 3,657,305; 3,234,252; 4,047,958; 3,427,271 and 2,846,458 are hereby incorporated herein by reference to further show methods for preparing the polydiorganosiloxane component of the compositions of this invention. It is to be understood that polydiorganosiloxanes that have been prepared in this preferred manner can contain small amounts of unreacted olefin and/or olefin-terminated polyoxyalkalene.

Component (d) is any cationic, nonionic or anionic organic surfactant suitable for preparing emulsions of the oil-in-water type and having an HLB value of from 8 to 18, inclusive. Examples of oil-in-water type surfactants include polyethoxylated quaternary ammonium salts and polyoxyethylene fatty amines as cationic surfactants, and polyethylene-glycol alkylethers, polyethyleneglycol alkylarylethers, polyethoxylated sorbitan monolaurate, polyethoxylated sorbitan monooleate, polyoxyethlene lanolin derivatives, and polyethoxylated fatty alcohols as nonionic surfactants. Mixtures of cationic and/or nonionic oil-in-water surfactants are also suitable. Other examples of suitable organic surfactants having an HLB value of from 8 to 18 may be found by consulting standard publications such as McCutcheon's "Detergents and Emulsifiers" 1975 North America Edition, MC Publishing Co., Glen Rock, N.J. 1975.

The amounts of components (a) and (b) that may be present in the compositions of this invention may vary widely and comprise, in total, from about 99.5 to about 91 percent by weight of the total weight of components (a) through (d). The aqueous solution (a) of astringent may comprise from about 89.5 to about 50, preferably from about 80 to about 65 weight percent of components (a) through (d); however, as noted above, an efficacious anti-perspirant should contain a sweat-reducing amount, preferably from about 10 to about 25 percent by weight, of the astringent agent itself. A preferred embodiment of this invention is a composition comprising from about 80 to about 65 percent by weight of an aqueous solution of astringent which consists of not more than about 50 weight percent astringent. The volatile liquid (b) comprises from about 10 to about 33 weight percent of the total weight of components (a) to (d).

The surfactant mixture, consisting essentially of components (c) and (d) comprises, in total, from about 0.5 to about 9 percent by weight of the total weight of components (a) and (d), with component (c) accounting for from about 0.4 to about 6 weight percent of the total of components (a) to (d).

The compositions of this invention may further comprise small amounts of non-essential components which are used in the cosmetic art. Examples of such components include colorants; perfumes; viscosity control additives, such as solvents or thickening agents for the continuous phase; and non-volatile organopolysiloxanes, such as polydimethylsiloxanes having a viscosity of from 10 to 10,000 centipoise at 25° C.

The compositions of this invention are suitable for use, without further processing, as a lotion, preferably packaged and dispersed as a roll-on-anti-perspirant composition. However, gel, aerosol and pump-spray formulations may be prepared therefrom using well-known adjuvants such as alcohols for gel-formation and solvents to reduce the viscosity of the formulation to less than 100 centipoise at 25° C. for aerosol and pump-spray use.

The compositions of this invention may be prepared by mixing the proper portions of the individual components in any order. Although the compositions of the invention are delineated in terms of an aqueous solution of an astringent (a) emulsified in a volatile liquid, (b), using a mixture of surfactants, (c) and (d), the following examples employ the preferred method of preparing a so-called aqueous phase comprising the aqueous solution of an astringent (a) and the oil-in-water type surfactant (d) and preparing a so-called oily phase comprising the volatile liquid (b) and the polydiorganosiloxane-polyoxyalkylene copolymer (c) and thereafter mixing the so-called aqueous phase with the so-called oily phase. Mixing may be done using standard emulsifying methods.

In order that those skilled in the art may better understand how the present invention can be practiced, the following specific components and examples are disclosed for purposes of illustrating and not limiting the invention. All percentages and parts are by weight, and all viscosities were measured in centipoise at 25° C.

EXPERIMENTAL

HYDROCARBON-MODIFIED POLYDIORGANOSILOXANEPOLYOXYALKYLENE COPOLYMERS

The copolymers used in the following Examples were prepared from trimethylsiloxy endblocked polysiloxanes containing methylhydrogensiloxane units having the general formula

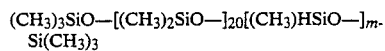

$(CH_3)_3SiO—[(CH_3)_2SiO—]_{20}[(CH_3)HSiO—]_m-Si(CH_3)_3$ having values of "m" as shown in Table I. These materials are readily prepared by equilibration of appropriate amounts of hexamethyldisiloxane, a cyclic telomer of dimethylsiloxy groups and a telomer of methylhydrogensiloxy groups as is well known in the art. The alkyl groups of the copolymers were derived from an alpha-olefin of the same number of carbon atoms as the alkyl group desired, and the polyoxyalkylene groups from an allylpolyoxyethylene glycol of 550 molecular weight (allyl PEG 550).

TABLE 1

| Co-polymer Number | Alkyl Group ($R^1$) | Polyether ($R^2$) | "m" Value of Starting Fluid | Nominal Formula |
|---|---|---|---|---|
| I | $C_{10}$ | allyl PEG 550 | 10 | $MD_{20}D'_8D_2M$ |
| II | $C_{14}$ | allyl PEG 550 | 8 | $MD_{20}D'_6D_2M$ |
| III | $C_{18}$ | allyl PEG 550 | 6 | $MD_{20}D'_4D_2M$ |

A known amount of starting polysiloxane containing methylhydrogensiloxy groups was charged to a reactor with an equal amount of toluene. The mixture was refluxed to remove toluene-water azeotrope, decanting and recycling the toluent to the reactor until the mixture was dry. The system was cooled to 100° C. and a small amount (about 1% on reactants) of a 0.2N solution of sodium acetate in methanol/isopropanol was added, followed by approximately 0.04% on reactants of a solution of chloroplatinic acid in octanol containing 3.5% platinum. Over a period of about an hour a quantity of alpha-olefin corresponding to the alkyl group desired in the product equal to 25% of the stoichiometric amount was fed to the reactor with stirring, followed by the stoichiometric amount of azeotropically dried (with toluene) allylpolyoxyethylene glycol of 550 molecular weight. Finally the balance of alpha-olefin plus a 10% molar excess was added over a period of about an hour. The mixture was held at 100° C. with stirring for an additional 4 hours. The toluene was then stripped under vacuum with heating until the temperature of the mixture reached 130° C. at 10 mm Hg pressure. The product was then cooled, filtered, and stored until used.

EXAMPLES 1-3

Liquid anti-perspirant composition were prepared using the following general recipe.

| Material | Parts by Weight |
| --- | --- |
| Water | 49.9 |
| Aluminum Zirconium tetrachlorohydrate Glycine salt (Wickenol 369) | 20.0 |
| Polysorbate 80 (Tween 80) | 0.1 |
| Cyclic Tetramer (predominantly octamethyl-cyclotetrasiloxane containing minor amounts of larger cyclics) | 29.0* |
| Organosilicon surfactant | 1.0* |
| | 100.0 |

*Certain surfactants were used as 10% active solutions in cyclic tetramer, in these cases quantities were adjusted accordingly.

The aluminum zirconium tetrachlorohydrate glycine salt was dissolved in the water and the Polysorbate 80 was added. The organosilicon surfactant was dissolved in the cyclic tetramer. The two solutions were mixed and homogenized in a Polytron.

The formulations were tested for "whitening" by applying equal quantities to different skin areas of a subject several times, observing the skin surface after drying and rating the whitening as "strong", "moderate", "very slight", and "none". The results are shown in Table II.

TABLE II

| Example | Organosilicon Surfactant | Whitening |
| --- | --- | --- |
| 1 | I | Very Slight |
| 2 | II | Very Slight |
| 3 | III | Very Slight |
| | Control A* | Strong |
| | Control B** | Strong |

*Control A utilized the commercial product DC-3225C made by Dow Corning which is believed to follow the teachings of U.S. Pat. Nos. 4,122,029 and 4,268,499.

EXAMPLE 4

A commercial roll-on anti-perspirant "Dry Idea" manufactured by the Gillette Company is a suspension comprising cyclic silicone, aluminum zirconium tetrachlorohydrate glycine salt, and a suspending agent. Surfactant III (2.5% by weight) was added to a portion of this product. The mixture was compared to the unmodified suspension, "Control C".

| | Whitening |
| --- | --- |
| Example 4 | Very Slight |
| Control C | Strong |

EXAMPLE 5

The effect on the stability on antiperspirant emulsions of varying the concentrations of organosilicon and organic surfactants was determined using the following general formulation

| Material | Parts by Weight |
| --- | --- |
| Cyclic Tetramer | 23.0 |
| Aluminum zirconium tetrachlorohydrate glycine salt | 20.0 |
| Polysorbate 80 | variable |
| Organosilicon surfactant | variable |
| Water | q.s. |
| TOTAL | 100.0 |

The results are displayed in Table III.

TABLE III

| Copolymer Number | Parts Copolymer | Parts Polysorbate 80 | Emulsion Stability |
| --- | --- | --- | --- |
| I | 1 | 0.2,0.4,0.75 | all stable |
| III | 1 | 0.2,0.4,0.75 | all unstable |
| I | 2 | 0.2,0.4,0.75 | all stable |
| III | 2 | 0.4,0.75 | marginally stable |
| III | 2 | 0.2 | unstable |
| I | 3 | 0.2,0.4,0.75 | all stable |
| III | 3 | 0.2,0.4,0.75 | all stable |

For the formulations studied in this Example it is apparent that Copolymer I ($C_{10}$ alkyl-modified) affords a wider formulation latitude than Copolymer III ($C_{18}$ alkyl-modified).

While the invention has been described in terms of various embodiments, those skilled in the art will recognize that modifications, substitutions and changes may be made without departing from the spirit of the invention. Accordingly, it is intended that the scope of the present invention be limited solely by the scope of the following claims.

What is claimed is:

1. An improved water-in-oil antiperspirant emulsion composition having a reduced whitening effect on skin, and including:
   (a) from about 89.5 to about 50 parts by weight of an aqueous solution of an astringent as a discontinuous phase;
   (b) from about 10 to about 45 parts by weight of a volatile liquid having a normal boiling point of less than 250° C. as a continuous phase, said volatile liquid being selected from the group consisting of methylsiloxane fluids having the average unit formula $$(CH_3)_a SiO_{(4-a)/2}$$

wherein a has an average value of from 2 to 3, inclusive;
   (c) from about 0.1 to about 3 parts by weight of an organic oil-in-water surfactant having an HLB value of from 8 to 18 inclusive,
wherein the improvement comprises (d) from about 0.4 to about 6 parts by weight of a polyorganosiloxane-polyoxyalkylene copolymer of the formula $$MD_x D'_y D''_z M$$

wherein
   D is $(CH_3)_2 SiO_{2/2}$,
   D' is $(CH_3)R^1 SiO_{2/2}$, where $R^1$ is an alkyl group having from 6 to 30 carbon atoms, D" is $(CH_3)R^2SiO_{2/2}$, where $R^2$ is a polyoxyalkylene ether residue of the formula

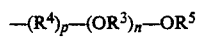

wherein each individual $R^3$ is an alkylene radical having 2 to 6 carbon atoms, $R^4$ is an alkylene radical having 2 to 20 carbon atoms, $R^5$ is hydrogen or an hydrocarbon radical of from 1 to about 12 carbon atoms, n has a value from about 5 to about 20, and p has a value of zero or 1, M is $(CH_3)_2R^6SiO_{2/2}$, where $R^6$ may be an alkyl group having from 1 to 30 carbon atoms or $R^2$, x has an average value of from about 10 to about 400, y has an average value of from 1 to about 200, and z has an average value of from 1 to about 100, and x+y+z has an average value of from about 12 to about 400, with the proviso that the weight ratio of $R^2$ to polysiloxane absent $R^2$ is from greater than 15/85 to less than 35/65; and the total of (a)+(b)+(c)+(d) being 100 parts by weight.

2. The antiperspirant emulsion composition of claim 1 wherein the volatile liquid is a mixture of cyclic dimethylsiloxanes consisting of octamethylcyclotetrasiloxane and larger cyclic dimethylsiloxanes.

3. The antiperspirant emulsion composition of claim 2 wherein the aqueous solution of an astringent antiperspirant agent consists of water and aluminum zirconium chloride tetrachlorohydrate glycine salt.

* * * * *